United States Patent [19]

Bonutti

[11] Patent Number: 5,549,683
[45] Date of Patent: Aug. 27, 1996

[54] ANTHROPLASTY COMPONENT

[76] Inventor: Peter M. Bonutti, 1303 W. Evergreen Plz., Effingham, Ill. 62401

[21] Appl. No.: 234,974

[22] Filed: Apr. 28, 1994

Related U.S. Application Data

[62] Division of Ser. No. 926,481, Aug. 6, 1992, Pat. No. 5,344,458.

[51] Int. Cl.$^6$ .................................. A61F 2/38; A61F 2/30
[52] U.S. Cl. .................................. 623/20; 606/73; 606/74; 623/18; 623/19
[58] Field of Search .................... 606/73, 74; 623/20, 623/16, 18, 22, 23

[56] References Cited

U.S. PATENT DOCUMENTS

| | | | |
|---|---|---|---|
| 4,038,704 | 8/1977 | Ring . | |
| 4,263,904 | 4/1981 | Jodet | 606/74 |
| 4,355,429 | 10/1982 | Mittelmeier et al. . | |
| 4,364,382 | 12/1982 | Mennen | 606/74 |
| 4,463,753 | 8/1984 | Gustilo | 606/73 |
| 4,640,271 | 2/1987 | Lower | 606/73 |
| 4,662,887 | 5/1987 | Turner et al. . | |
| 4,769,040 | 9/1988 | Wevers . | |
| 4,778,469 | 10/1988 | Lin et al. . | |
| 4,865,607 | 9/1989 | Witzel et al. . | |
| 4,892,552 | 1/1990 | Ainsworth et al. . | |
| 4,919,671 | 4/1990 | Karpf . | |
| 4,963,152 | 10/1990 | Hofmann et al. . | |
| 4,963,153 | 10/1990 | Noseberger et al. . | |
| 5,064,439 | 11/1991 | Chang et al. . | |
| 5,180,383 | 1/1993 | Haydon | 606/73 |
| 5,259,398 | 11/1993 | Vrespa | 906/73 |

FOREIGN PATENT DOCUMENTS

| | | | |
|---|---|---|---|
| 2595241 | 9/1987 | France | 623/22 |
| 2660546 | 10/1991 | France | 623/22 |
| 0663893 | 11/1988 | Switzerland | 623/22 |
| 719625 | 3/1980 | U.S.S.R. . | |
| 757159 | 8/1980 | U.S.S.R. . | |

Primary Examiner—David Isabella
Attorney, Agent, or Firm—Tarolli, Sundheim, Covell, Tummino & Szabo

[57] ABSTRACT

An arthroplasty component is positioned relative to a bone by engaging a first side of the bone with a first tab on the arthroplasty component. Thereafter, the arthroplasty component is pivoted about a location where the first tab engages the first side of the bone. A second tab on the arthroplasty component is moved along a second side of the bone while the arthroplasty component is pivoted about the location where the first tab engages the first side of the bone. A tray portion of the arthroplasty component is positioned over a portion of the bone disposed between the first and second sides of the bone while the arthroplasty component is pivoted about the location where the first tab engages the first side of the bone. In one embodiment of the invention, a keel is moved into the bone at a location between the sides of the bone while the arthroplasty component is pivoted about the location where the first tab engages the first side of the bone. A fastener may be moved through the second tab, a portion of the bone and into the keel portion of the arthroplasty component to retain the arthroplasty component against movement relative to the bone.

37 Claims, 7 Drawing Sheets

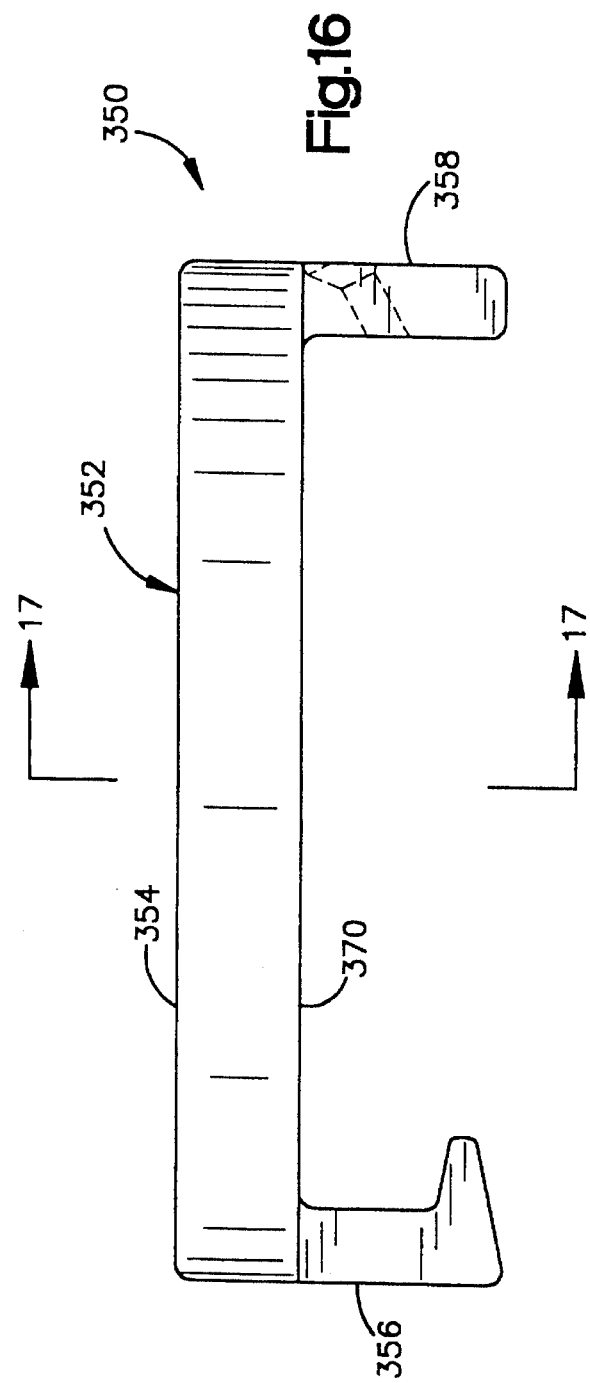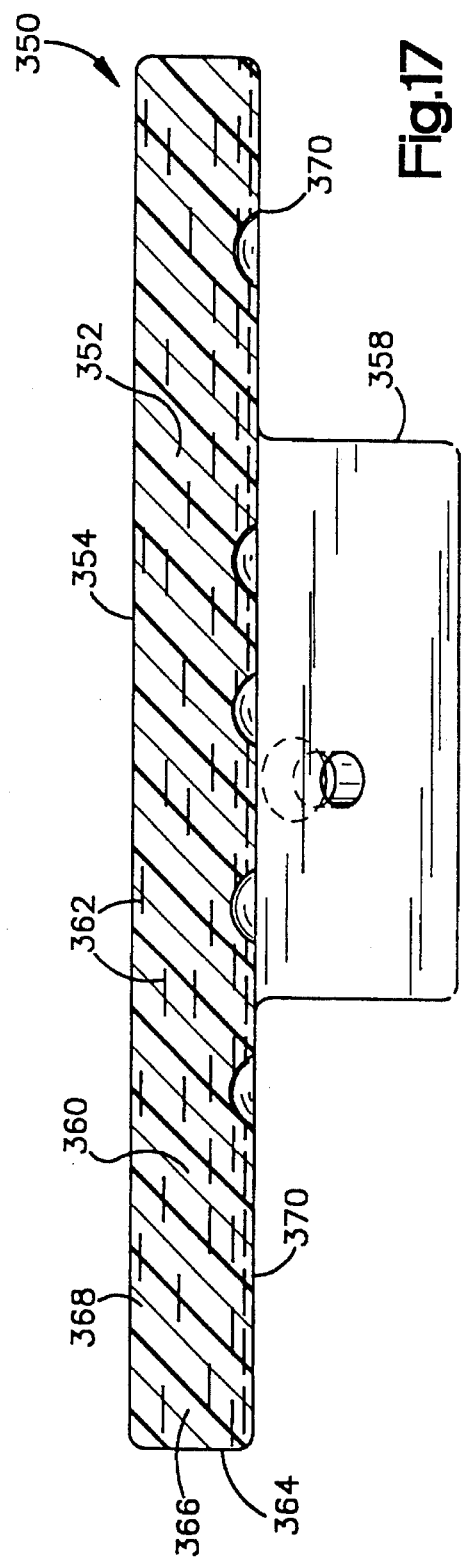

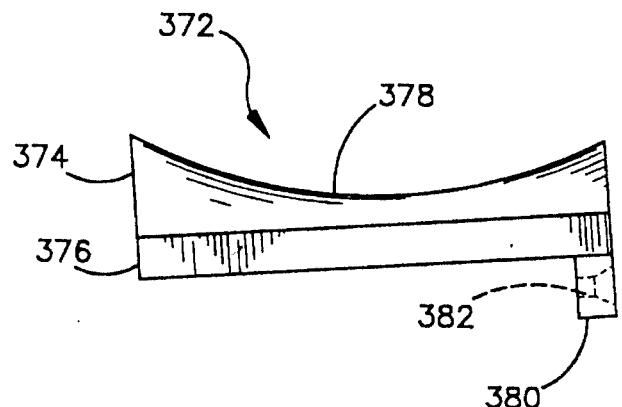
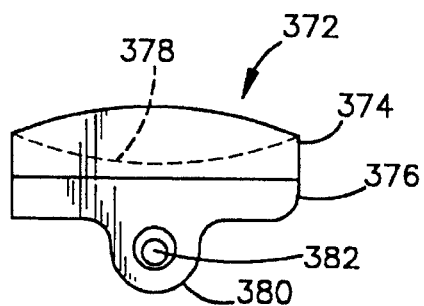
Fig.18    Fig.19
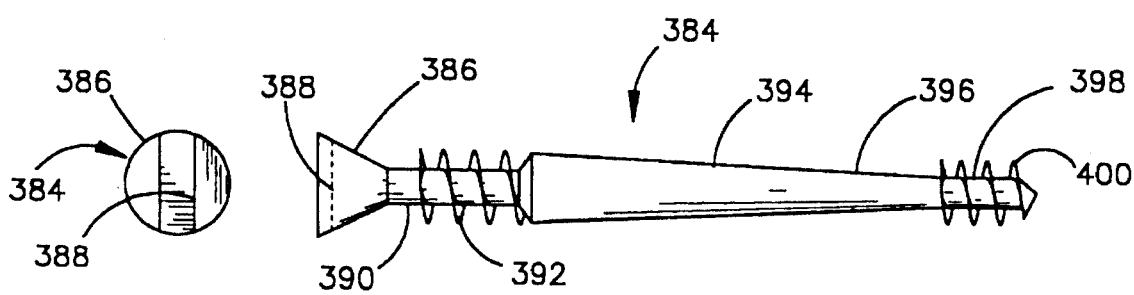
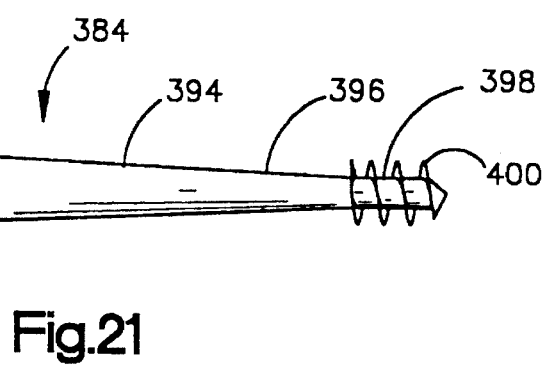
Fig.20    Fig.21
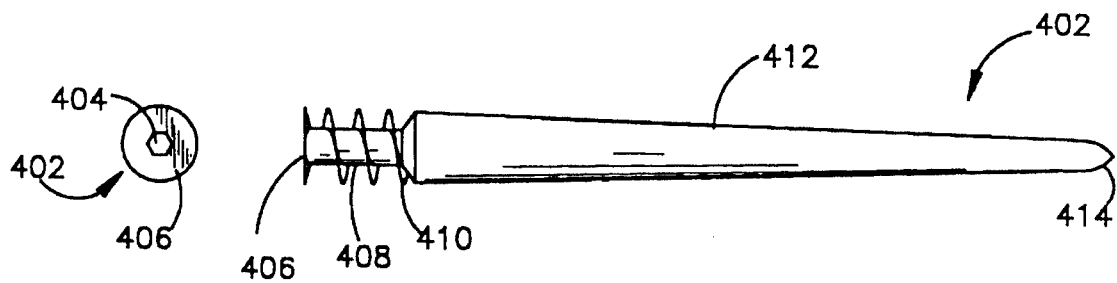
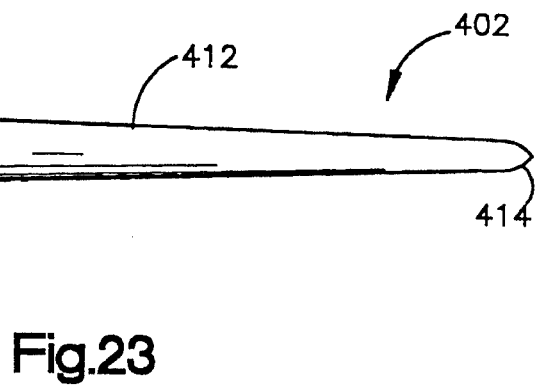
Fig.22    Fig.23

ANTHROPLASTY COMPONENT

This is a divisional of application Ser. No. 07/926,481 filed on Aug. 6, 1992, now U.S. Pat. No. 5,344,458.

BACKGROUND OF THE INVENTION

The present invention relates to an arthroplasty component. More particularly, the present invention relates to an arthroplasty component for capping a bone, such as a glenoid component for use in shoulder arthroplasty.

DESCRIPTION OF THE PRIOR ART

Arthroplasty is the reshaping or reconstructing of a diseased or damaged joint. The procedure may require use of artificial joint components to replace natural joint portions. Some natural joint portions are replaced with components having a tray portion with an articulating surface for engagement with a head portion of a long bone (or its replacement). Such joint portions include the tibia and the glenoid process of the scapula (or the "glenoid bone").

The glenoid bone is funnel-shaped, having an outer (distal) end surface which is the articulating surface, and an outer side surface extending proximally from the outer end surface. A typical glenoid component is fixed to the glenoid bone using bone cement and an intramedullary keel. This type of fixation often fails, because the intramedullary keel is located in soft cancellous bone rather than hard cortical bone. This type of fixation is also difficult and traumatic, because of the need to drill an opening for the intramedullary keel in a direction generally normal to the articulating surface of the glenoid bone. Such drilling requires a large exposure of the joint, and complex and difficult to use tools.

It would thus be desirable to have a glenoid component which can be fixed to the glenoid bone in a different manner, and preferably without the need for bone cement. It is desirable to avoid bone cement because the body may react to the cement. There is a higher incidence of infection when bone cement is used. Also, bone cement can fatigue and break. Particles of bone cement can break off and cause further destruction in the joint. Further, fractures can propagate easily in bone cement, so that a small area of damage to a layer of bone cement will result in total failure of the layer of bone cement.

SUMMARY OF THE INVENTION

The present invention is an arthroplasty component for affixation to a bone having an outer end surface and an outer side surface. The component has a tray portion for overlying an end surface of the bone. The tray portion has portions extending from the tray portion for engaging the outer side surface of the bone to block movement of the tray portion in a first direction on the bone.

In a preferred embodiment, the present invention is a glenoid component for affixation to a glenoid bone having an outer end surface and an outer side surface, the glenoid component being engageable by a humeral part. The glenoid component includes a tray portion for overlying the axial end surface or articulating surface of the glenoid bone. The tray portion has an outer major side surface for engagement with the humeral part, an inner major side surface for engagement with the outer end surface of the glenoid bone, and an outer periphery. A first tab extends axially from the outer periphery of the tray portion for engagement with the outer side surface of the glenoid bone. A second tab extends axially from the outer periphery of the tray portion for engagement with the outer side surface of the glenoid bone. The tabs hold the glenoid component in place on the glenoid bone.

The glenoid component may also include fastener means such as a screw engageable with one of the first and second tabs and extensible transversely through the outer side surface of the glenoid bone for securing the glenoid component to the glenoid bone.

The glenoid component of the present invention is highly advantageous as compared to typical glenoid components which use cement and an intramedullary keel. The present glenoid component is easier to implant because it uses an anterior fastener in place of the standard intramedullary keel. Less soft tissue damage occurs because of the simpler exposure required. Minimal bone resection is required, as no intramedullary opening must be formed. The component has improved stability in shear, torsion, and anterior-posterior lift off.

Further, because of the secure fixation resulting from the engagement of the tabs on the hard cortical material of the glenoid bone, there is usually no need to cement the glenoid component onto the glenoid bone. This allows for decreased glenoid offset, which is advantageous, and also for the use of bone ingrowth material. If bone cement is used, texturing on the inner major side surface of the component limits propagation of cracks in the bone cement. The optional screw fixation which may extend into the anterior bone cortex or may be transcortical provides even further stability. There is no need to have a 90° angle glenoid screw, as is sometimes used to secure a glenoid component. There is no need to use angled burrs or reamers to drill central openings.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 16 is an elevational view of a reinforced implant;

FIG. 17 is a sectional view taken along line 17—17 of FIG. 16;

FIG. 18 is a side elevational view of another tibial tray in accordance with the present invention;

FIG. 19 is a front elevational view of the tibial tray of FIG. 18;

FIG. 20 is an end view of another bone screw in accordance with the present invention;

FIG. 21 is an elevational view of the bone screw of FIG. 20;

FIG. 22 is an end view of a third bone screw in accordance with the present invention; and FIG. 23 is an elevational view of the bone screw of FIG. 22.

DESCRIPTION OF PREFERRED EMBODIMENT

Figure 1:
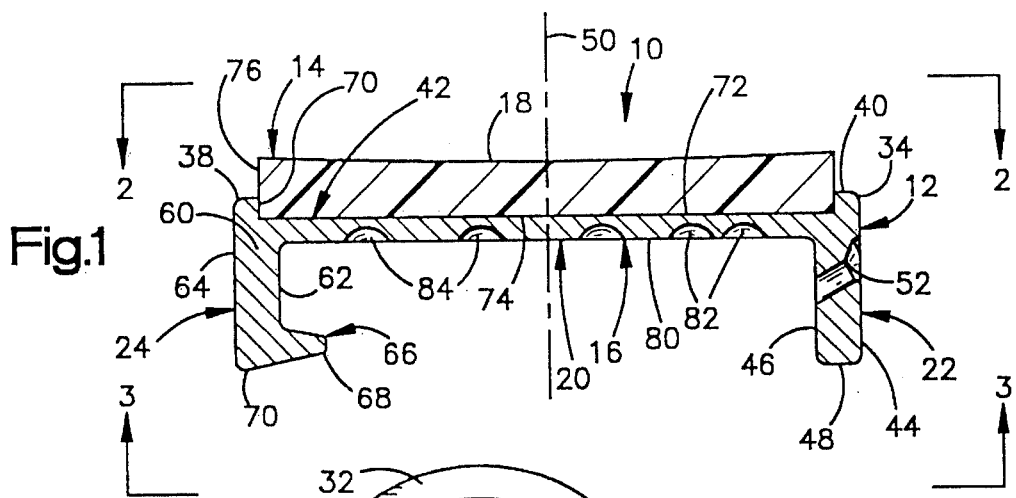
FIG. 1 is a sectional view, taken along line 1—1 of FIG. 3, of a glenoid component for capping a glenoid bone in shoulder arthroplasty.

The present invention relates to a joint component for use in arthroplasty. The present invention is applicable to various joint component constructions. As representative of the present invention, FIG. 1 illustrates a glenoid component 10. The glenoid component 10 includes a metal base 12 and a plastic insert 14. The metal base 12 has a lower major side surface 16 for placement adjacent to the articulating surface of a glenoid bone (not shown). The plastic insert 14 has a concave upper major side surface 18 for articulation with a humeral part of the glenohumeral joint when the glenoid component 10 caps the glenoid bone.

Figure 2:
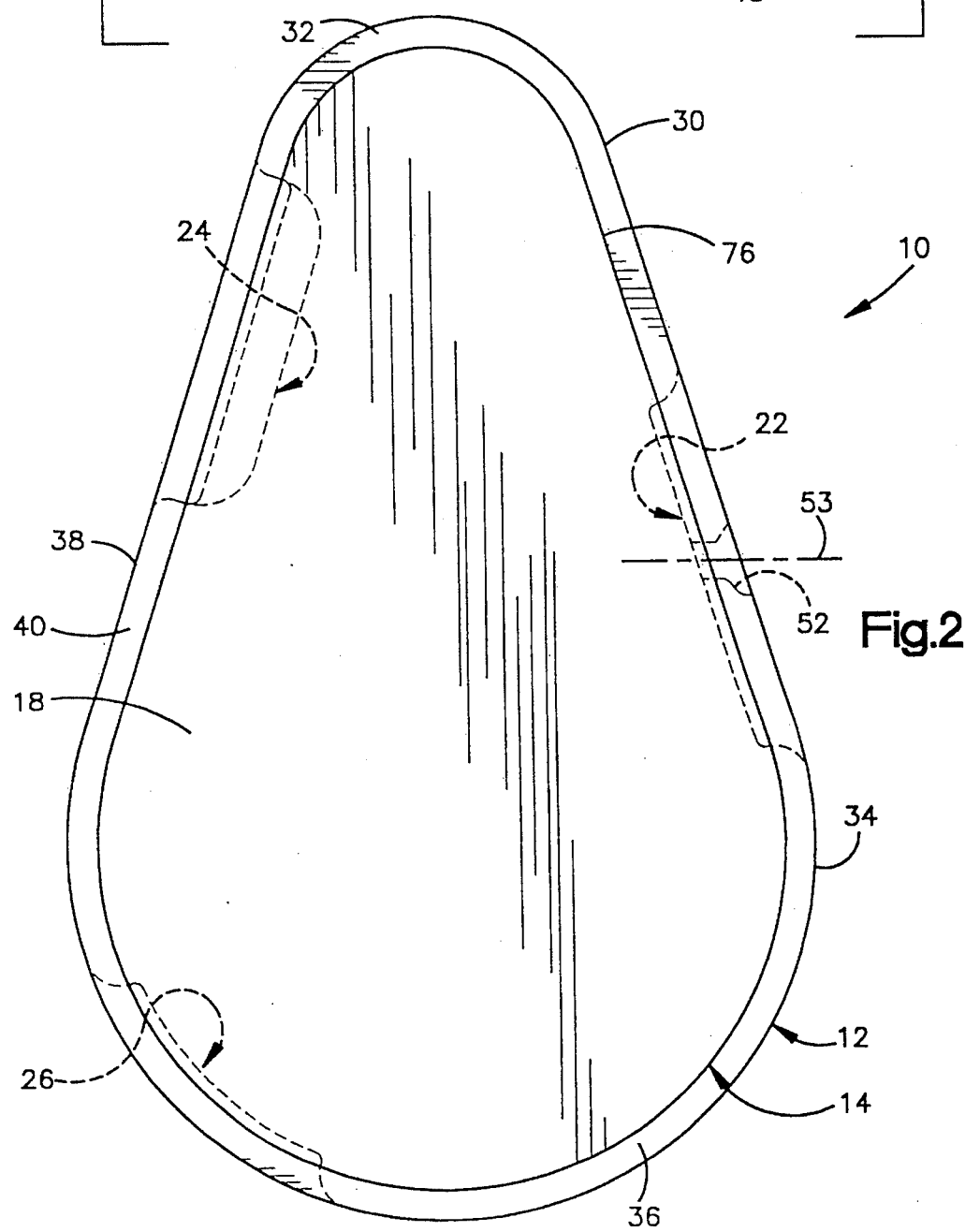
FIG. 2 is a top plan view of the glenoid component of FIG. 1.

The metal base 12 includes a tray portion 20 with an outer periphery 30 (FIG. 2) which is the outer periphery of the glenoid component 10. The metal base 12 has an upper peripheral portion 32, an anterior peripheral portion 34, a lower peripheral portion 36, and a posterior peripheral portion 38. The tray portion 20 of the glenoid component 10 has an upper major side surface 40.

The plastic insert 14 is received in a cut-out 42 in the upper surface of the base tray portion 20. The cut-out 42 is sized to snugly receive the plastic insert 14, in a known manner. The cut-out 42 is defined by an edge surface 70 and a major side surface 72. The plastic insert 14 has a lower side surface 74 in engagement with the surface 72 of the metal base 12, and an outer side surface 76 in engagement with the edge surface 70 of the cut-out 42 in the metal base 12.

The metal base 12 has three integral tabs projecting proximally (down as viewed in FIG. 1) from the tray portion 20. These include an anterior tab 22, an upper posterior tab 24, and a lower posterior tab 26.

The anterior tab 22 (FIG. 1) projects downwardly as viewed in FIG. 1 from the anterior peripheral portion 34 of the tray portion 20 of the metal base 12. The anterior tab 22 extends generally normal to the tray portion 20 of the metal base 12, in a direction parallel to an axis 50 of the glenoid component 10. The anterior tab 22 has an outer side surface 44, an inner side surface 46, and a lower side surface 48 connecting the inner side surface and the outer side surface.

A screw hole 52 extends at an angle through the anterior tab 22.

The lower posterior tab 26 (FIG. 3) is generally similar to the anterior tab 22. The lower posterior tab 26 projects downwardly as viewed in FIG. 1 from the lower peripheral portion 36 of the tray 20. The lower posterior tab 26 has an outer surface 54, an inner surface 56, and a lower side surface 58 joining them.

The upper posterior tab 24 has a support portion 60 (FIG. 1) having an inner side surface 62 and an outer side surface 64. A hook portion 66 extends transversely from the support portion 60 inwardly toward the anterior tab 22 in a direction transverse to the axis 50 of the glenoid component 10. The hook portion 66 has a relatively sharp distal end portion 68 joined by a lower side surface 70 to the outer side surface 64 of the support portion 60.

It should be noted that the anterior tab 22 and the posterior tabs 24 and 26 can be located elsewhere on the periphery 30 of the glenoid component 10. Further, the tabs 22, 24 and 26 may have different lengths and/or configurations, so long as they serve the function of blocking lateral movement of the tray portion 20 by engagement with the outer side surface of the glenoid bone. The length of the anterior tab 22 along the periphery of the glenoid component 10 is selected so as to substantially block movement of the tray portion 20 in a first direction relative to the glenoid bone, when the anterior tab 22 engages an outer side surface of the glenoid bone. Similarly, the upper posterior tab 24 and the lower posterior tab 26 are located and dimensioned so as to substantially block movement of the tray portion 20 of the glenoid component 10 relative to the glenoid bone in a second direction. There may also be a different number of tabs provided, or even one tab extending partially or completely around the periphery 30 of the glenoid component 10.

Figure 3:
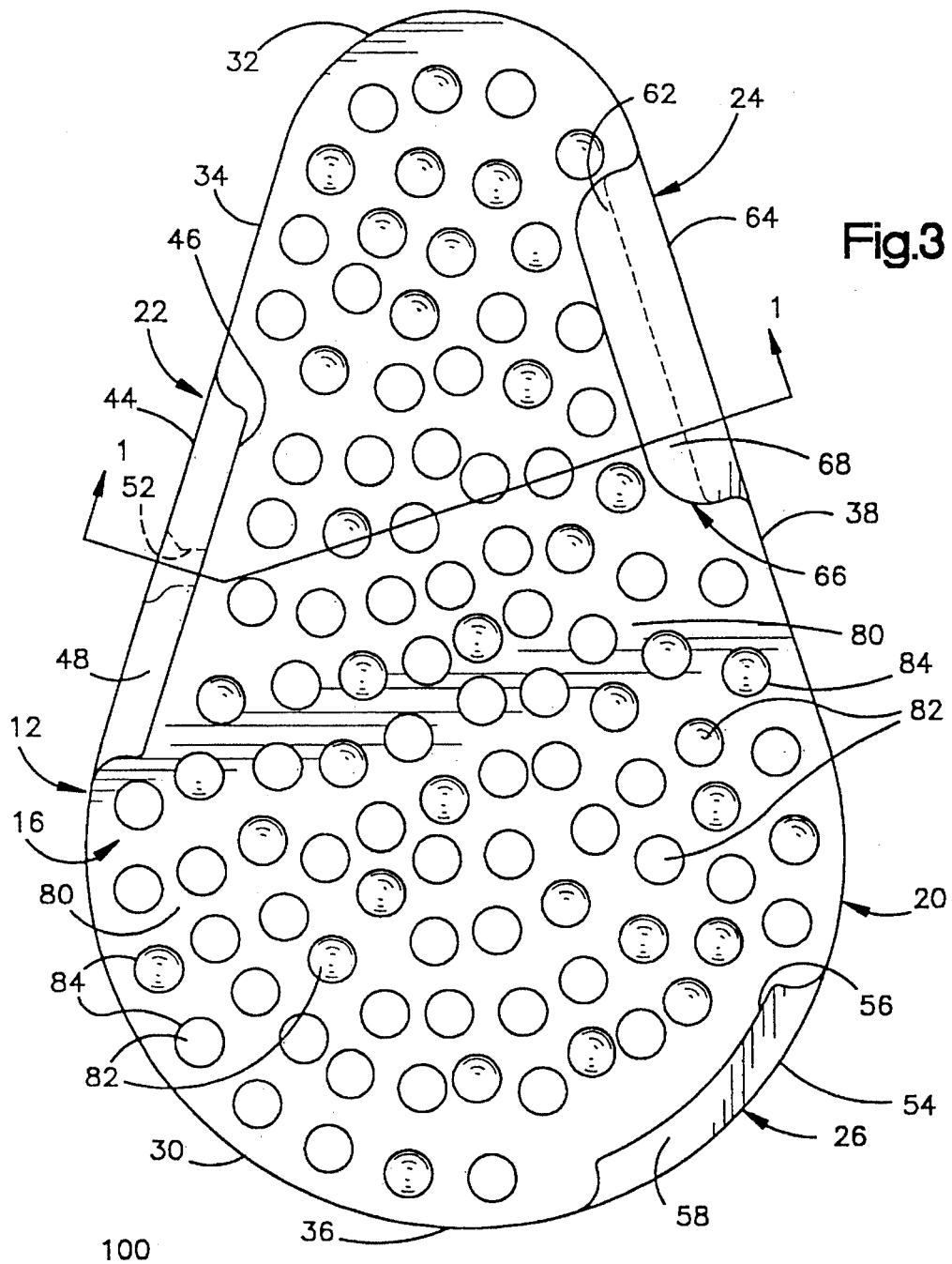
FIG. 3 is a bottom plan view of the glenoid component of FIG. 1.

The lower major side surface 16 of the tray portion 20 includes an axially outward web surface 80 (FIG. 3). The lower major side surface 16 also includes a plurality of spherical surfaces 82 defining a plurality of dimples 84 in the tray portion 20. In a preferred embodiment, the dimples 84 are two to three millimeters in diameter.

Figure 4:
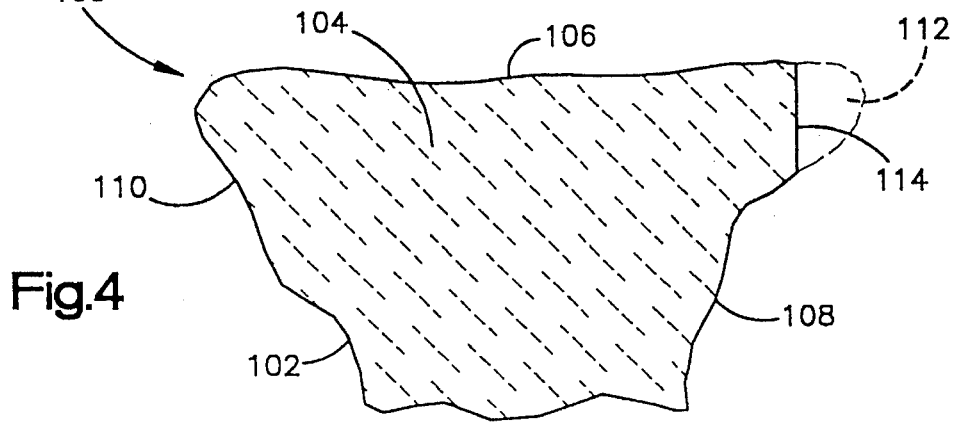
FIG. 4 is a schematic illustration of a glenoid bone prior to capping.
Figure 5:
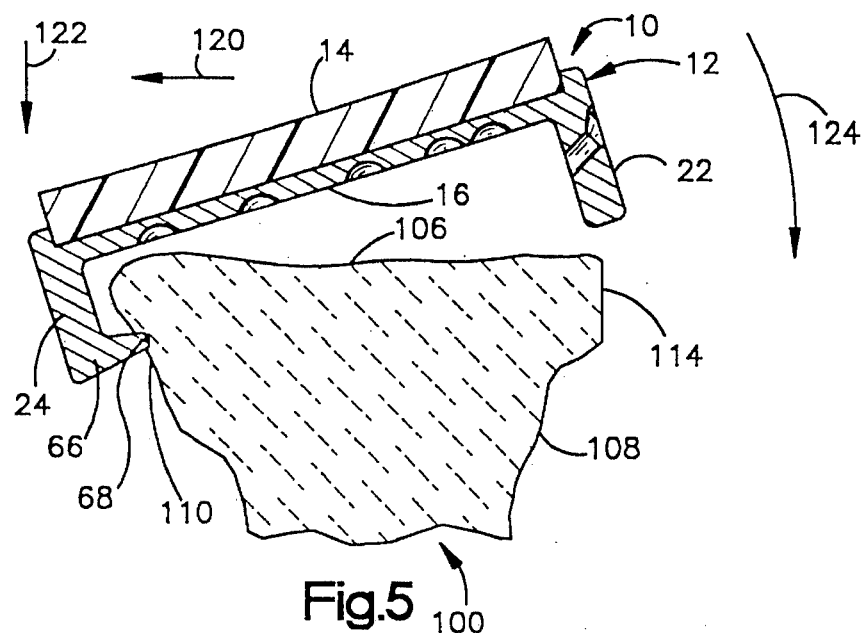
FIG. 5 is a schematic illustration of the glenoid bone of FIG. 4 with the glenoid component of FIG. 1 in a partially inserted position.
Figure 6:
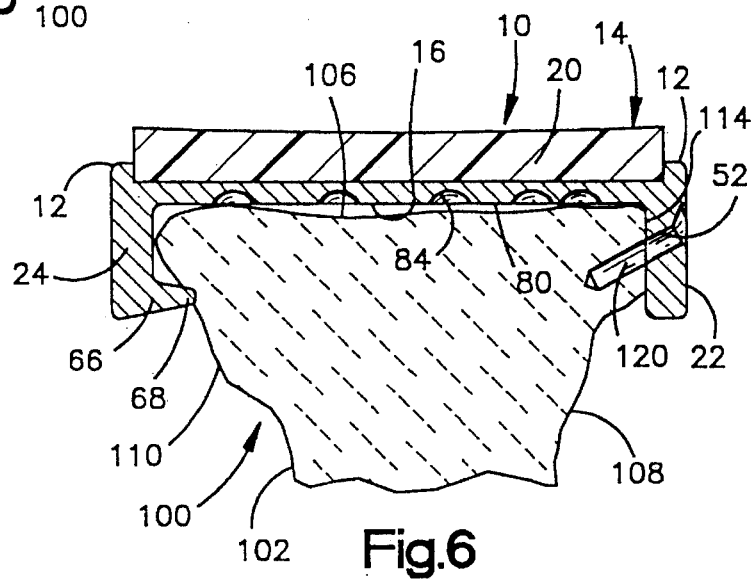
FIG. 6 is a schematic illustration of the glenoid bone of FIG. 4 after capping with the glenoid component of FIG. 1.

The glenoid component 10 is usable in capping a glenoid bone, such as the glenoid bone 100 illustrated schematically in FIGS. 4–6. The glenoid bone 100 is funnel-shaped and has a neck portion 102 extending inwardly from the end portion 104. The end portion 104 has an articulating surface 106 which may be cut back if desired to accommodate the thickness of the glenoid component 10. The glenoid bone has an anterior outer side surface 108 and a posterior outer side surface 110.

FIGS. 5 and 6 illustrate the securing of the glenoid component 10 to the glenoid bone 100. After the joint is exposed anteriorly, the glenoid component 10 is slid between the parts of the joint, from anterior to posterior, in a direction as indicated by the arrow 120. When the posterior tabs 24 and 26 of the glenoid component 10 are posterior to the glenoid bone 100, the posterior tabs are slid proximally relative to the glenoid bone 100 in a direction as indicated by the arrows 122.

The hook portion 66 of the upper posterior tab 24, with its end portion 68, is engaged with the posterior outer side surface 110 of the glenoid bone 100 as shown in FIG. 5. The glenoid component 10 is then pivoted about the hook portion 66, in the direction indicated by the arrow 124, from the position shown in FIG. 5 to the position shown in FIG. 6. In the position shown in FIG. 6, the lower major side surface 16 of the glenoid component 10 is adjacent to or in engagement with the articulating surface 106 of the glenoid bone 100. The anterior tab 22 is in engagement with the anterior outer side surface 108 of the glenoid bone 100. The lower posterior tab 26 (not shown in FIGS. 4–6) is also in engagement with the posterior outer side surface 110 of the glenoid bone 100.

A fastener, such as a screw 120, may then optionally be inserted through the screw hole 52 in the anterior tab 22 of the metal base 12. The screw 120 engages in the hard cortical bone on the anterior portion of the glenoid bone 100. Alternatively, the fastener may extend across the glenoid bone 100 and terminate in the cortical bone on the posterior side of the glenoid bone. Suitable holes may be drilled in the glenoid bone 100 to receive the fastener, as necessary. It is contemplated that a glenoid component in accordance with the present invention will likely be fixed to the glenoid bone with a screw such as the screw 120. However, this may not in all cases be necessary, and so the present invention also contemplates capping with the tabs only, without a separate fastener.

The tabs 22, 24 and 26 block both lateral and axial movement of the tray portion 20 of the glenoid component 10 relative to the glenoid bone 100. The anterior to posterior dimension of the glenoid bone 100 may be shortened, prior to capping, by resecting an anterior edge portion 112 (FIG. 4) of the glenoid bone 100, so that the glenoid component 10 snaps into position on the glenoid bone 100 and is retained snugly in position thereon. It should be understood that the steps recited above for positioning the glenoid component 10 or the glenoid bone 100 may and likely will be varied, as the surgeon moves and works the glenoid component into place on the glenoid bone, to the position shown in FIG. 5 and then the position shown in FIG. 6.

The hook 66 on the posterior lip 24 provides a pivot point for mounting of the glenoid component 10 on the glenoid bone 100. The hook 66 also blocks axial outward movement of the glenoid component 10 from the bone 100.

The tabs 22, 24 and 26 on the glenoid component 10 engage hard cortical bone material at the outer surface of the bone 100. The cortical bone is less likely to wear away and loosen the grip of the tabs on the bone, than is cancellous bone. Thus, the fixation obtained by the present invention is superior to that obtained by a central (intramedullary) keel which is in soft cancellous bone.

The anterior and posterior tabs 22, 24 and 26 engage the glenoid bone 100 at locations spaced from the center of the bone. The tabs are thus working through a longer lever arm to resist rotation of the glenoid component 10 on the bone. For this reason also, the stability obtained by the present invention is superior to that obtained by a central keel.

Because component fixation is obtained at the outer edges of the bone with the present invention, no intramedullary screws are needed to affix the component. This eliminates the possibility of metal screw heads wearing on the under surface of a plastic insert, which is a known cause of component failure. It also eliminates the need for a thicker metal component to accommodate the screw fixation. Any screw fixation in the present invention is obtained laterally through the outer side surface of the glenoid bone into hard cortical bone, which is clearly superior.

The metal base 12 of the glenoid component 10 is preferably titanium or cobalt chrome two to three millimeters thick. The plastic insert 14 is preferably polyethylene or polyetheretherketone about three millimeters thick. Thus, the total thickness of the glenoid component is about five to six millimeters. This is in contrast to the normal glenoid component which is eleven millimeters thick. The glenoid component of the present invention can be made thinner because no fixation need be obtained along the tray portion, fixation rather being obtained at the side of the bone.

Figure 7:
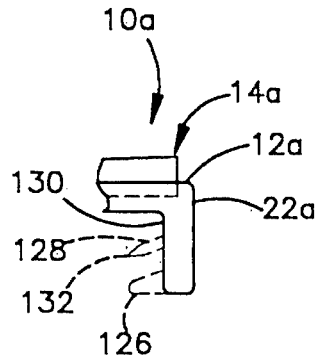
FIG. 7 is a fragmentary view of a glenoid component having a modified anterior tab.

FIG. 7 illustrates alternative configurations for an anterior tab 22a of a glenoid component 10a. The anterior tab 22a may include a hook portion 126 similar to the hook portion 66 (FIG. 1) of the posterior tab 24. The anterior tab 22a may include a post 128 formed integrally with the anterior tab 22a, and extending inwardly from an inner side surface 130 of the tab 22a to a pointed end portion 132. The post 128 could replace the screw 120.

Figure 8:
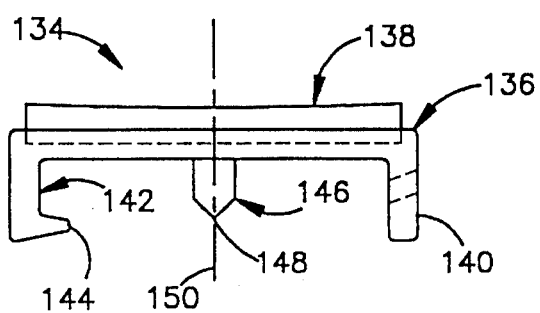
FIG. 8 illustrates a glenoid component modified by the addition of a solid central keel.

FIG. 8 illustrates another alternative configuration for a glenoid component in accordance with the present invention. The glenoid component 134 includes a metal base 136 with a plastic insert 138. The metal base 136 has an anterior tab 140 and one or more posterior tabs 142, which may have a hook portion 144. A small intramedullary keel 146 is provided with a pointed distal end portion 148 extending along the axis 150 of the glenoid component 134. Upon movement of the glenoid component 134 into position on a glenoid bone, as illustrated in FIGS. 5 and 6, the keel 146 embeds in the intramedullary bone to further assist in stabilizing the glenoid component 134 on the glenoid bone.

Figure 9:
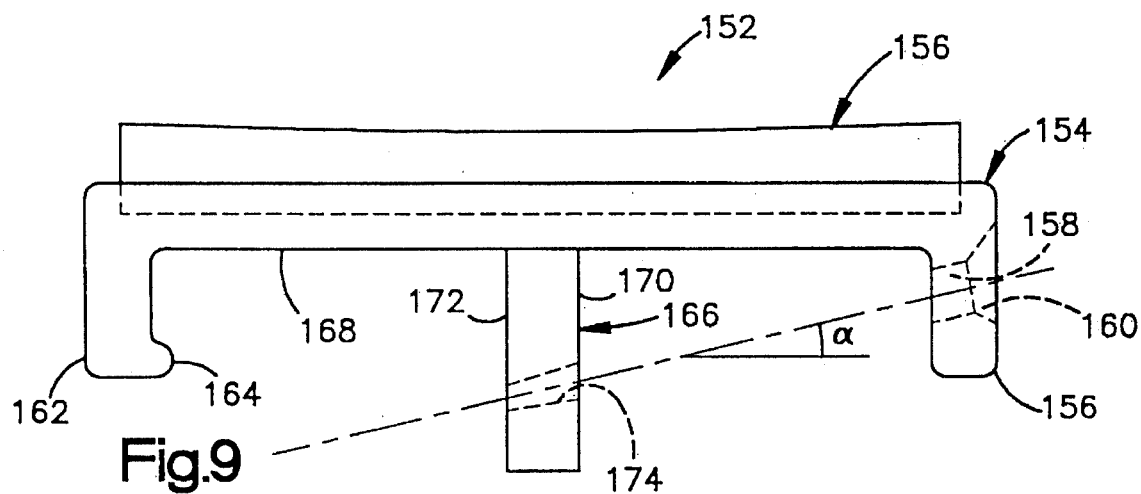
FIG. 9 illustrates a glenoid component modified by the addition of a central keel having a tapered opening therein.
Figure 10:
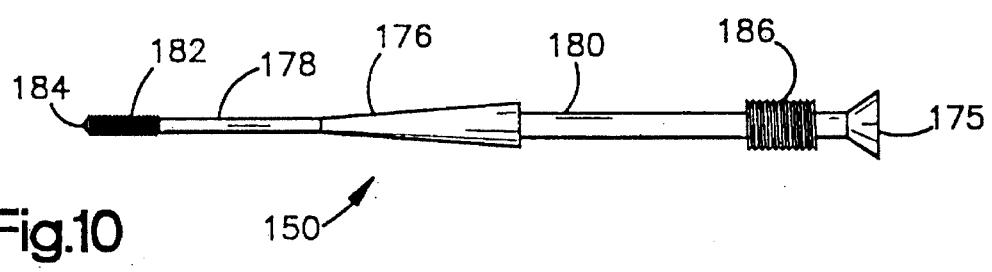
FIG. 10 is an elevational view of a screw for use with the glenoid component of FIG. 9.
Figure 11:
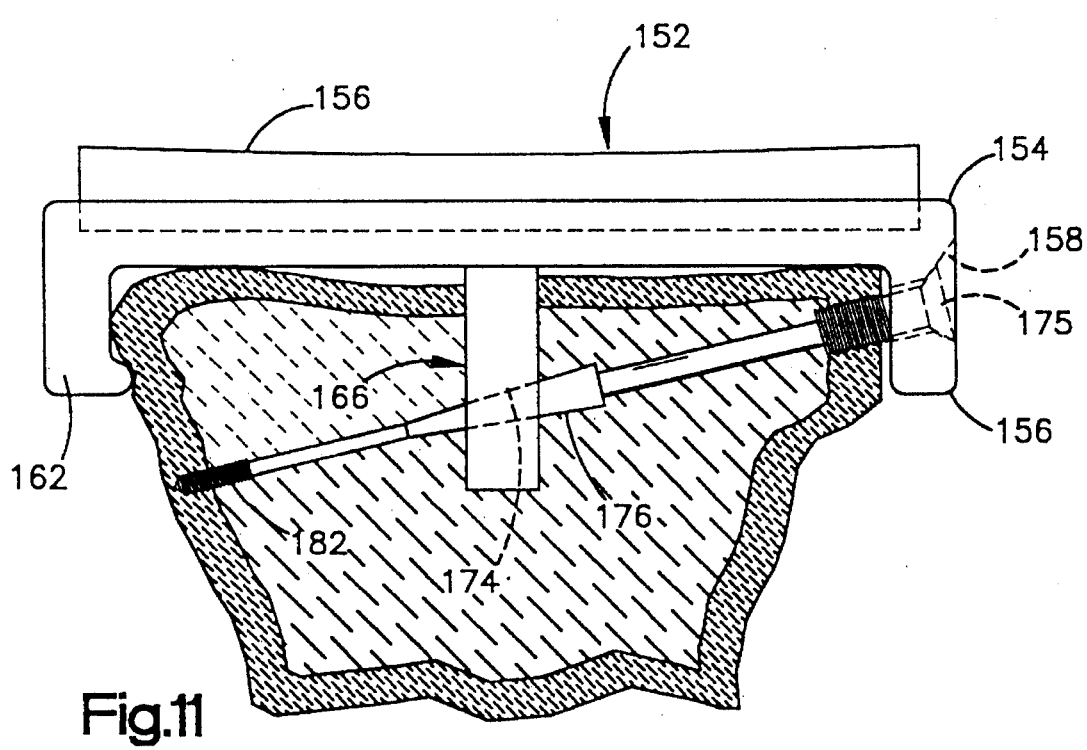
FIG. 11 is an assembly view of the parts of FIGS. 9 and 10.

FIGS. 9–11 illustrate another embodiment of the present invention in which a transcortical screw 150 assists in securing a glenoid component 152 to a glenoid bone. The glenoid component 152 has a metal base 154 and a plastic insert 156. The base 154 has an anterior tab 156 with a screw hole 158 extending therethrough. The screw hole 158 is countersunk at 160. The base 154 also has a posterior tab 162 with a hook portion 164.

A central keel 166 extends axially from a tray portion 168 of the base 154. The keel 166 has an anterior side surface 170 and a posterior side surface 172. A tapered opening 174 extends transversely through the keel 166 from the anterior side surface 170 to the posterior side surface 172. The opening 174 has a standard Morse taper.

The screw 150 (FIG. 10) has a head portion 175 for engagement with the countersunk portion 160 of the screw hole 158. A tapered shank portion 176 of the screw 150 is disposed intermediate a distal shank portion 178 and a proximal shank portion 180 of the screw 150. The shank portion 176 has a Morse taper matching that of the opening 174 in the keel 166 of the component 152. The screw 150 has a distal threaded portion 182 adjacent the distal end 184 of the screw 150. A proximal threaded portion 186 is disposed on the proximal shank portion 180 adjacent the screw head 154.

The glenoid component 152 is first placed over the glenoid bone (shown schematically in FIG. 11) as described above. A through hole is drilled for the screw 150. The screw 150 is inserted through the screw hole 158 in the anterior tab 156 of the glenoid component 152. The various portions of the screw 150 are dimensioned so that, as the distal and proximal threaded portions 182 and 186 draw the screw head 175 snugly into engagement with the anterior tab 156, the tapered screw portion 176 engages in the tapered opening 174 in the keel 166. The interlocking between the screw 150 and the keel 166 further aids in stability, especially rotational stability, of the glenoid component 152 on the glenoid bone. It should be noted that either the proximal threaded portion 186 or the distal threaded portion 186 may be omitted, and that they may have different thread pitches as desired. For example, the thread portion 182 is illustrated as having a finer pitch than the threaded portion 186.

The screw 150 extends at an angle α relative to the plane of the glenoid component 152. The angle α is selected so as to provide the minimum amount of lift off and the maximum amount of rotational stability, while still maintaining anterior exposure only and cortical rather than medullary fixation. This same angle is used with the screw 120 (FIG. 6) for holding the glenoid component 10 in place on the glenoid bone 100. The angle α is preferably about 10°.

Figure 12:
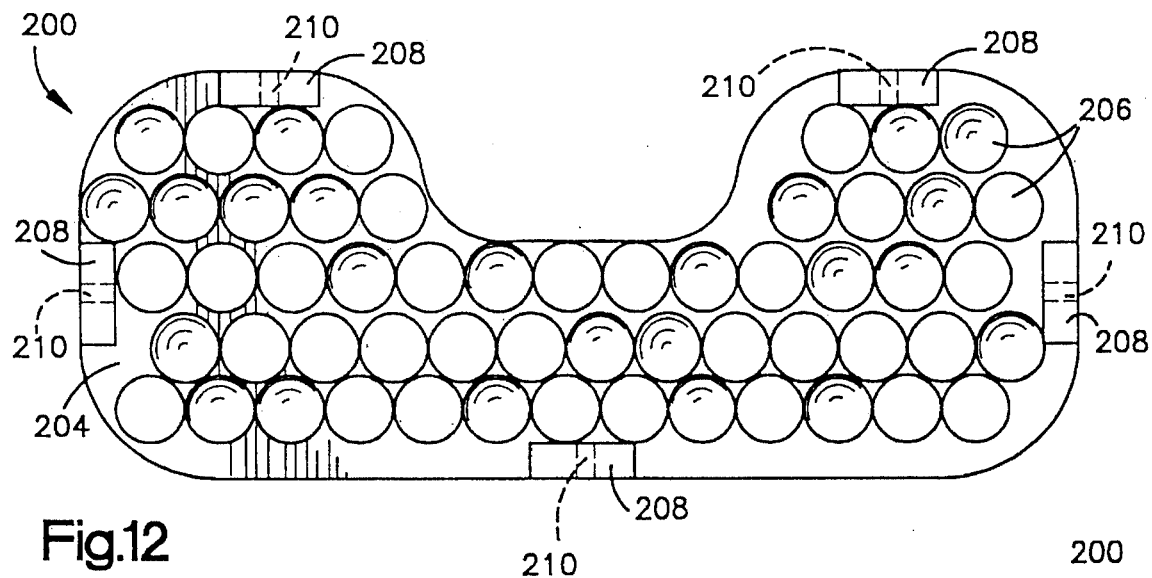
FIG. 12 is a bottom plan view of a tibial component for capping a tibia in knee arthroplasty.
Figure 13:
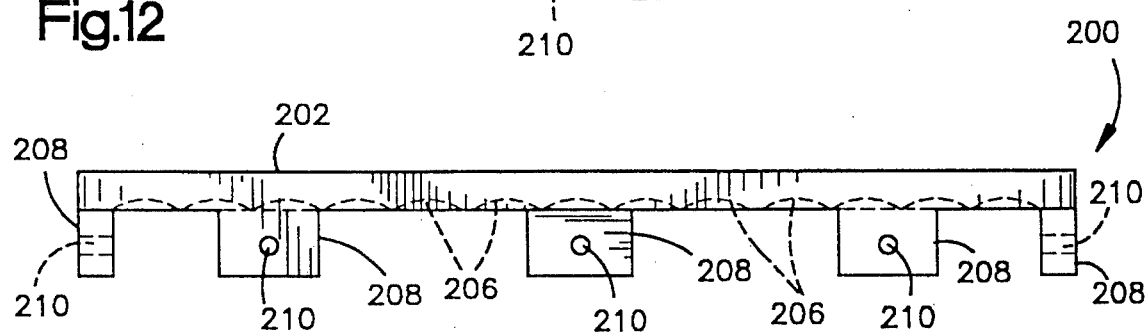
FIG. 13 is an elevational view of the tibial component of FIG. 12.

The present invention is applicable to joints other than the glenohumeral joint. Other joints which have bones which may be capped in accordance with the present invention include (without limitation) the knee, ankle, wrist, and hip (acetabulum). As an example, FIGS. 12 and 13 illustrate a tibial tray 200 having an articulating surface 202 and a lower major side surface 204. The lower major side surface 204 has a plurality of two millimeter diameter dimples or depressions 206. A plurality of tabs 208 extend downwardly from the lower major side surface 204 of the tibial tray 200. The tabs 208 are engageable with an outer side surface of the tibia bone (not shown) to block movement of the tibial component 200 relative to the tibia. Fastener openings 210 may be provided in the tabs 208 for optional screw fixation laterally through cortical bone of the tibia. The number, dimensions, and placement of the tabs 208 may be selected to give best securing of the tibial tray 200 to the tibia.

Although the foregoing description has referenced cementless installation of arthroplasty components, it is also contemplated that bone cement may be used if desired by the surgeon. The texturing of the lower side surfaces of the illustrated components is useful in this regard. Bone cement is applied between the end surface of the bone to be capped and the lower major side surface of the component. The bone cement flows mainly into the dimples or impressions on the lower side surface of the component, and also may form a thin layer on the web surface of the component. For example, the bone cement when applied between the articulating surface 106 (FIG. 6) of the glenoid bone 100 and the lower major side surface 16 of the glenoid component 10, would flow into the dimples 84, and possibly lie on the web surface 80. Thus, any cracks which would form in the bone cement would tend to propagate only to or through one dimple 84, and then stop. This can potentially avoid cracks spreading through the entire extent of the layer of bone cement and thus destroying the efficacy of the cement.

Figure 14:
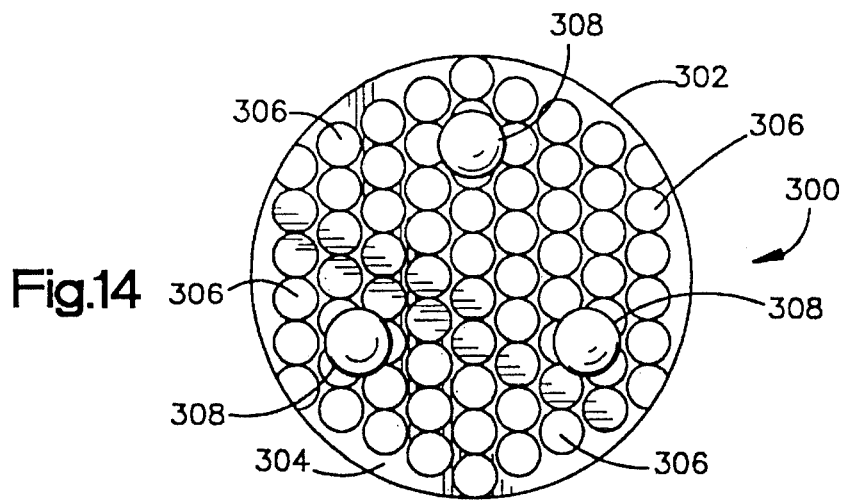
FIG. 14 is a bottom plan view of a patellar implant in accordance with the present invention.
Figure 15:
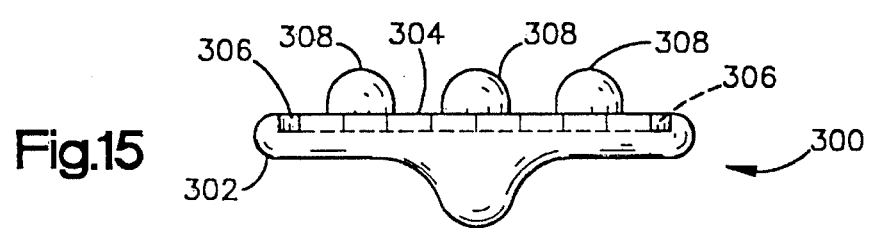
FIG. 15 is an elevational view of the patellar implant of FIG. 14.

A further example of an arthroplasty component in accordance with the present invention is the patellar implant 300 illustrated in FIGS. 14 and 15. The implant 300 has a tray portion 302 with a web surface 304 surrounding a plurality of dimples 306. Three posts 308 project from the tray portion 306. When the implant 300 is affixed to a patella, the majority of the bone cement applied between the surface of the patella and the tray portion 302 flows into the dimples 306 rather than lying on the web surface 304. Thus, any cracks which might develop in the bone cement are limited to the individual packets of bone cement within the dimples 306.

The present invention also relates to a method of capping a bone in arthroplasty such as shoulder arthroplasty. The joint is first exposed anteriorly so that there is two to three centimeters of space at the anterior side of the joint, between the glenoid bone 100 and the humeral head (not shown). The glenoid component 10 (FIGS. 5 and 6) is then inserted between the glenoid bone 100 and the humeral head in a posterior direction, as indicated by the arrow 120, with the posterior lips 24 and 26 of the glenoid component 10 being inserted first. The glenoid component 10 is inserted until the posterior lips 24 and 26 of the glenoid component are posterior to the glenoid bone 100. The posterior lips 24 and 26 of the glenoid component 10 are slid proximally down onto the outer side surface 110 of the glenoid bone 100. The hook 66 on the posterior lip 24 engages the outer side surface 110 of the glenoid bone 100 and may make a small impression therein.

The glenoid component 10 is then pivoted, in the direction indicated by the arrow 124, into the capped position shown in FIG. 6. The anterior lip 22 snaps around the glenoid bone 100 to engage the anterior outer side surface 108 of the glenoid bone 100 at a location spaced from the posterior lips 24 and 26. The lower major side surface 16 of the tray portion 20 is adjacent to or engaged with the articulating surface 106 of the glenoid bone 100.

If the glenoid bone 100 is too large in diameter to fit between the anterior and posterior lips of the glenoid component 10, a small anterior portion of the glenoid bone may be removed as shown at 144, prior to capping with the anterior lip 22. There is desirably a very snug fit between the glenoid component 10 and the glenoid bone 100. This can be achieved by sizing the glenoid bone 100 and the glenoid component 10 so that the surgeon must exert some force to affix the glenoid component to the glenoid bone.

The surgeon then inserts a fastener such as a screw 120 through the screw opening 52 in the anterior lip 22. The screw 120 seats in the hard cortical bone material at the side of the glenoid bone. In this condition, the anterior and posterior tabs and the screw block movement of the tray portion 20 and the entire glenoid component 10 relative to the bone 100. Because of the secure fixation of the glenoid component 10, a central keel is not needed.

As illustrated above, one typically uses a two-material implant (metal and plastic) to obtain different functions of the two different materials at different locations on the implant. A low coefficient of friction is needed at the joint (articulating) surface, because it is bearing on metal. Thus, plastic is chosen for the upper portion or insert of the implant. Strength and rigidity are needed for the base, in contact with and securing the articulating surface to the bone. Thus, metal is chosen for the base.

The tibial tray 200 (FIGS. 12 and 13), unlike the glenoid component 10 illustrated in FIGS. 1–5, is made of only one piece rather than a metal base and a plastic insert. A glenoid component, or other arthroplasty component in accordance with the present invention, may similarly be made of only one piece of material rather than two pieces bonded or snapped together. For a glenoid component, this would typically be a plastic material rather than a metal material.

Although all-plastic implants are known and used, applicant has found that plastics which are best suited to function as an articulating surface are not well suited to function as a base. Polyethylene, for example, which is suitable as an articulating surface, is too soft and flexible and is not rigid enough over time to present a stable surface for bone to bond to. Also, such plastics can fail when screwed into bone.

Thus, all-plastic inserts are always cemented to the bone. However, bone cement does not provide a stable long-term method of fixation. Also, if bone cement is used, bone ingrowth material can not be used. Bone ingrowth material such as hydroxyapatite (HA) or tricalcium phosphate (TCP) will not stick to known bone implant polymers such as polyethylene. Thus, it is not possible to augment the body's natural bone growth function at the junction between the implant and the bone. Accordingly, the all-plastic (one-material) implants available today are deficient in all these regards.

Applicant has found, however, that polyetheretherketone (PEEK) is a suitable material for an all-plastic implant. Applicant has found that PEEK, when reinforced with fibers (to form a composite material) is strong enough to replace the metal portion of a typical implant. It can if necessary be screwed into the bone. And, importantly, it is rigid enough and maintains its rigidity over time so that it presents a stable surface for bone to bond to.

Since composites can be as stiff or as flexible as needed, a portion of the PEEK implant can be left unreinforced or only slightly reinforced. Unreinforced PEEK has a coefficient of friction which is acceptably low for a joint surface, that is, a coefficient of friction about twice that of polyethylene. Thus, unreinforced PEEK is suitable for articulation.

Thus, it is possible to provide a one-material insert having a varying modulus from proximal to distal—rigid and strong at the bone surface, and smooth at the articulating surface.

Applicant has also found that bone ingrowth material can be bonded to PEEK and will stick. Thus, it is possible to provide an implant of plastic (specifically, PEEK) and bond a bone ingrowth surface to the lower major side surface (and outer side surfaces also) of the implant. This will make the implant cementless, as the bone ingrowth material promotes rapid bone ingrowth and thus substitutes for the cement.

The implant can be made entirely of PEEK reinforced as desired. Alternatively, the implant can be made of another polymer such as polysulfone or PAEK (polyaryletherketone), reinforced with fibers to form a composite. Suitable fibers include carbon fibers and aramid (Kevlar®) fibers. The implant can also be a base made from PEEK preferably reinforced with an insert made from another material such as polyethylene.

The bone ingrowth material can be bonded on as a layer 50–100 microns thick, or in the form of a mesh or beaded surface with 150–400 micron bead porosity. Known techniques for bonding bone ingrowth material, such as plasma spraying, can be used, perhaps at a low temperature.

FIGS. 16 and 17 illustrate an arthroplasty component 350 for capping a bone such as a glenoid bone or a tibia. The component 350 can be implanted in the manner described above. The component 350 has a tray portion 352 with an articulating surface 354 and has two tab portions 356 and 358 for fixation to cortical bone material.

The component 350 is made of a body 360 of PEEK reinforced with fibers 362. The fibers 362 are densest at the proximal portion 364 of the component 350. Thus, the portion 364 of the component 350 is very strong, strong enough to be attached and stabilized to the bone. The fibers 362 are less dense at a central portion 366 of the component 350. There are no fibers 362 in the distal portion 368 of the component 350, adjacent the articulating surface 354. Thus, the portion 368 of the component 350 is suitable to provide the articulating surface 354. The component 350 has a layer of bone ingrowth material 370 bonded to it, in the manner and for the purposes discussed above.

FIGS. 18 and 19 illustrate another tibial tray in accordance with the present invention. The tibial tray 372 includes a plastic insert 374 fixed to a metal base 376. The insert 374 has a hollowed out articulating surface 378. The base has a projecting tab 380 which extends along the outer side surface of a tibia (shown in phantom). A screw hole 382 may be formed in the tab 380 to receive therethrough a screw (not show) for fixation to the tibia. Additional tabs like the tab 380 may be provided, having a fixed pin attached thereto (or formed therewith), a screw hole, or no additional attachment features.

FIGS. 20–23 illustrate other fixation screws for use in implant fixation in accordance with the present invention. The screw 384 (FIGS. 20–21) has a head 386 with a driver slot 388. A large diameter shank portion 390 extends from the head 386. A thread convolution 392 is formed on the large diameter shank portion 390. A tapered portion 394 having a truncated conical outer surface 396 extends from the large diameter shank portion 390. The tapered portion 394 is smaller in diameter than the thread convolution 392. A small diameter shank portion 398 extends from the tapered portion 394. A thread convolution 400 is formed on the small diameter shank portion 398. The tapered portion 394 is engageable with an opening in a keel in an implant (not shown) as in FIGS. 9–11.

The screw 402 (FIGS. 22–23) does not have a radially enlarged head but instead has a hex driver opening slot 404 in the proximal end surface 406 of a constant diameter shank portion 408. A thread convolution 410 is formed on the constant diameter shank portion 408. A tapered portion 412 extends from the large diameter shank portion 390 and terminates in a pointed distal end 412. The tapered portion 412 is smaller in diameter than the thread convolution 410. The tapered portion 412 is engageable with an opening in a keel in an implant (not shown) as in FIGS. 9–11.

From the above description of the invention, those skilled in the art will perceive improvements, changes and modifications in the invention. Such improvements, changes and modifications within the skill of the art are intended to be covered by the appended claims.

I claim:

1. A method of positioning an arthroplasty component relative to a bone, said method comprising the steps of providing an arthroplasty component having a tray portion with a first tab extending from one side of the tray portion and a second tab extending from another side of the tray portion, engaging a first side of the bone with the first tab on the arthroplasty component, thereafter, pivoting the arthroplasty component about a location where the first tab engages the first side of the bone, moving the second tab on the arthroplasty component along a second side of the bone while performing said step of pivoting the arthroplasty component about the location where the first tab engages the first side of the bone, and positioning the tray portion of the arthroplasty component over a portion of the bone disposed between the first and second sides of the bone while performing said step of pivoting the arthroplasty component about the location where the first tab engages the first side of the bone.

2. A method as set forth in claim 1 further including the step of moving a fastener through the second tab on the arthroplasty component and into the bone with a longitudinal central axis of the fastener extending at an acute angle to a side of the tray portion of the arthroplasty component.

3. A method of positioning an arthroplasty component relative to a bone, said method comprising the steps of providing an arthroplasty component having a tray portion with a first tab extending from one side of the tray portion, a second tab extending from another side of the tray portion and a keel which extends from the arthroplasty component at a location between the first and second tabs, engaging a first side of the bone with the first tab on the arthroplasty component, thereafter, pivoting the arthroplasty component about a location where the first tab engages the first side of the bone, moving the second tab on the arthroplasty component along a second side of the bone while performing said step of pivoting the arthroplasty component about the location where the first tab engages the first side of the bone, moving the keel into the bone at location between the first and second sides of the bone while performing said step of pivoting the arthroplasty component about the location where the first tab engages the first side of the bone, positioning the tray portion of the arthroplasty component over a portion of the bone disposed between the first and second sides of the bone while performing said step of pivoting the arthroplasty component about the location where the first tab engages the first side of the bone, and moving a fastener through the second tab, through a portion of the bone, and into the keel to retain the arthroplasty component against movement relative to the bone.

4. A method of positioning an arthroplasty component relative to a bone, said method comprising the steps of providing an arthroplasty component having a tray portion with a first tab extending from one side of the tray portion and a keel which extends from the tray portion of the arthroplasty component, positioning the arthroplasty component relative to the bone with the tray portion extending across an end surface on the bone and the first tab extending along a first outer side of the bone which extends transverse to the end surface on the bone, said step of positioning the arthroplasty component relative to the bone includes moving the keel through the end surface on the bone into the bone, and applying force to the arthroplasty component urging the tray portion of the arthroplasty component toward the end surface on the bone and urging the first tab toward the first outer side of the bone, said step of applying force to the arthroplasty component including moving a fastener through the first tab and then into the bone along a path which is skewed at an acute angle to the end surface on the bone, said step of moving the fastener through the first tab and into the bone along a path which is skewed at an acute angle to the end surface on the bone includes moving the fastener into the keel.

5. A method of positioning an arthroplasty component relative to a bone, said method comprising the steps of providing an arthroplasty component having a tray portion and a projecting portion extending from the tray portion, positioning the arthroplasty component relative to the bone with the tray portion extending across an end surface on the bone and the projecting portion disposed in engagement with the bone and extending transversely to the end surface on the bone, and interconnecting the arthroplasty component and the bone with a fastener, said step of interconnecting the arthroplasty component and the bone including moving the fastener through the projecting portion of the arthroplasty component, moving the fastener through a cortical portion of the bone on a first side of the bone, moving the fastener through a cancellous portion of the bone, moving the fastener into a cortical portion of the bone on a second side of the bone, engaging the cortical portion of the bone on the first side of the bone with a first thread convolution on the fastener, engaging the cortical portion of the bone on the second side of the bone with a second thread convolution on the fastener, and applying force to the arthroplasty component with the fastener during performance of said steps of engaging the cortical portion of the bone on the first side of the bone with a first thread convolution and engaging the cortical portion of the bone on the second side of the bone with a second thread convolution to urge the tray portion of the arthroplasty component toward the end surface on the bone, said step of applying force to the arthroplasty component including moving the fastener along a path which is skewed at an acute angle to the end surface on the bone.

6. A method as set forth in claim 3 wherein said step of moving the fastener into the keel includes transmitting force from the fastener to the keel to urge the tray portion of the arthroplasty component toward the portion of the bone disposed between the first and second sides of the bone.

7. A method as set forth in claim 3 wherein said steps of moving the fastener through the second tab, through a portion of the bone, and into the keel includes moving the fastener along a path which is skewed at an acute angle to a side of the arthroplasty component.

8. A method as set forth in claim 3 wherein said step of engaging a first side of the bone includes engaging the first side of the bone with a hook portion of the first tab at a location offset from the portion of the bone which is disposed between the first and second sides of the bone.

9. A method as set forth in claim 3 wherein said step of moving the second tab on the arthroplasty component along the second side of the bone includes increasing area of engagement of the second tab with the second side of the bone during at least a portion of said step of pivoting the arthroplasty component about a location where the first tab engages the first side of the bone.

10. A method as set forth in claim 3 further including interconnecting the portion of the bone disposed between the first and second sides of the bone and the tray portion of the arthroplasty component with bone cement.

11. A method as set forth in claim 7 wherein said step of interconnecting the portion of the bone disposed between the first and second sides of the bone and the tray portion of the arthroplasty component with bone cement includes filling a plurality of recesses in a side of the tray portion with bone cement to retard subsequent propagation of cracks through the bone cement.

12. A method as set forth in claim 4 wherein the arthroplasty component has a second tab which extends from the tray portion, said step of positioning the arthroplasty component relative to the bone including engaging a second side of the bone with the second tab and pivoting the arthroplasty component about a location where the second tab engages the second side of the bone.

13. A method as set forth in claim 4 wherein said step of applying force to the arthroplasty component includes applying force against the keel with the fastener to transmit force from the fastener through the keel to the tray portion of the arthroplasty component urging the tray portion of the arthroplasty component toward the end surface on the bone.

14. A method as set forth in claim 13 wherein said step of applying force to the arthroplasty component includes applying force against the first tab with the fastener to transmit force from the fastener through the first tab to the tray portion of the arthroplasty component urging the tray portion of the arthroplasty component toward the end surface on the bone.

15. A method as set forth in claim 4 wherein said step of moving the fastener through the first tab and into the bone along a path which is skewed at an acute angle to the end surface on the bone includes moving the fastener through a cortical portion of the bone on the first side of the bone and moving the fastener through the keel on the arthroplasty component and a cancellous portion of the bone into a cortical portion of the bone on a second side of the bone.

16. A method as set forth in claim 15 wherein said step of applying force to the arthroplasty component includes engaging the cortical portion of the bone on the first side of the bone with a thread convolution and engaging the cortical portion of the bone on the second side of the bone with a thread convolution.

17. A method as set forth in claim 4 further including interconnecting the end surface on the bone and the tray portion of the arthroplasty component with bone cement, said step of interconnecting the end surface on the bone and the tray portion of the arthroplasty component with bone cement includes filling a plurality of recesses in a side of the tray portion with bone cement to retard subsequent propagation of cracks through the bone cement.

18. A method as set forth in claim 5 wherein said step of positioning the arthroplasty component relative the bone includes pivoting the arthroplasty component about a location where the portion of the arthroplasty component engages the second side of the bone and positioning the tray portion of the arthroplasty component relative to the end surface of the bone while performing said step of pivoting the arthroplasty component about a location where a portion of the arthroplasty component engages the second side of the bone.

19. A method as set forth in claim 5 wherein the projecting portion of the arthroplasty component is a tab which projects from side of the tray portion of the arthroplasty component, said step of positioning the arthroplasty component relative to the bone includes engaging the cortical portion of the bone on the first side of the bone with the projecting portion of the arthroplasty component, said steps of moving the fastener through the cortical portion of the bone on the first side of the bone, moving the fastener through the cancellous portion of the bone, and moving the fastener into a cortical portion of the bone on the second side of the bone being performed after moving the fastener through the projecting portion of the arthroplasty component.

20. A method of positioning an arthroplasty component relative to a bone, said method comprising the steps of providing an arthroplasty component having a tray portion with a first tab extending from a first side of the tray portion, a second tab extending from a second side of the tray portion and a keel extending from a central portion of the tray portion, said keel extending from the tray portion for a distance which is greater than a distance which the second tab extends from the tray portion, engaging a first side of the bone with the first tab on the arthroplasty component, thereafter, pivoting the arthroplasty component about a location where the first tab engages the first side of the bone, moving the keel into a cancellous portion of the bone while performing said step of pivoting the arthroplasty component about the location where the first tab engages the first side of the bone, moving the second tab along a second side of the bone while performing said step of pivoting the arthroplasty component about the location where the first tab engages the first side of the bone, and, thereafter, moving a fastener through the first tab, through a cortical portion of the bone on the first side of the bone and into the keel portion of the arthroplasty component along a path which is skewed at an acute angle to the tray portion of the bone.

21. A method as set forth in claim 20 further including the steps of engaging the cortical portion of the bone on the first side of the bone with a first thread convolution on the fastener and engaging the cortical portion of the bone on the second side of the bone with a second thread convolution on the fastener.

22. A method as set forth in claim 20 wherein said step of moving the fastener into the keel portion of the arthroplasty component includes engaging the keel portion of the arthroplasty component with the fastener and transmitting force from the fastener to the keel portion of the arthroplasty component urging the tray portion of the arthroplasty component against the bone.

23. A method of positioning an arthroplasty component relative to a bone, said method comprising the steps of providing an arthroplasty component having a tray portion and a projecting portion extending from the tray portion, the projecting portion of the arthroplasty component is a keel which extends from a central portion of the tray portion of the arthroplasty component, positioning the arthroplasty component relative to the bone with the tray portion extending across an end surface on the bone and the projecting portion disposed in engagement with the bone and extending transversely to the end surface on the bone, said step of positioning the arthroplasty component relative to the bone includes positioning the arthroplasty component with the projecting portion extending into a cancellous portion of the bone, and interconnecting the arthroplasty component and the bone with a fastener, said step of interconnecting the arthroplasty component and the bone including moving the fastener through the projecting portion of the arthroplasty component, moving the fastener through a cortical portion of the bone on a first side of the bone, moving the fastener through a cancellous portion of the bone, moving the fastener into a cortical portion of the bone on a second side of the bone, engaging the cortical portion of the bone on the first side of the bone with a first thread convolution on the fastener, and engaging the cortical portion of the bone on the second side of the bone with a second thread convolution on the fastener, said step of moving the fastener through the projecting portion of the arthroplasty component being performed after moving the fastener through the cortical portion of the bone on the first side of the bone and prior to initiation of said step of moving the fastener into the cortical portion of the bone on the second side of the bone.

24. A method of positioning an arthroplasty component relative to a bone, said method comprising the steps of providing an arthroplasty component having a tray portion with a first tab extending from one side of the tray portion a second tab extending from another side of the tray portion and a projection extending from the tray portion at a location between the first and second tabs, engaging a first side of the bone with the first tab on the arthroplasty component, thereafter, pivoting the arthroplasty component about a location where the first tab engages the first side of the bone, moving the projection from the tray portion into the bone at a location between the first side of the bone and a second side of the bone while performing said step of pivoting the arthroplasty component about the location where the first tab engages the first side of the bone, moving the second tab on the arthroplasty component along the second side of the bone while performing said step of pivoting the arthroplasty component about the location where the first tab engages the first side of the bone, and positioning the tray portion of the arthroplasty component over a portion of the bone disposed between the first and second sides of the bone while performing said step of pivoting the arthroplasty component about the location where the first tab engages the first side of the bone.

25. A method as set forth in claim 24 further including the step of moving a fastener through at least one of the tabs on the arthroplasty component and into the projecting portion of arthroplasty component with a longitudinal central axis of the fastener extending at an acute angle to a side of the tray portion of the arthroplasty component.

26. A method of positioning an arthroplasty component relative to a bone, said method comprising the steps of providing an arthroplasty component having a tray portion with a first tab extending from one side of the tray portion and a second tab extending from another side of the tray portion, engaging a first side of the bone with the first tab on the arthroplasty component, thereafter, pivoting the arthroplasty component about a location where the first tab engages the first side of the bone, moving the second tab on the arthroplasty component along a second side of the bone while performing said step of pivoting the arthroplasty component about the location where the first tab engages the first side of the bone, positioning the tray portion of the arthroplasty component over a portion of the bone disposed between the first and second sides of the bone while performing said step of pivoting the arthroplasty component about the location where the first tab engages the first side of the bone, and moving a fastener through the second tab on the arthroplasty component, through a cortical portion of the bone on the second side of the bone, through a cancellous portion of the bone located between the first and second sides of the bone and into engagement with a cortical portion of the bone on the first side of the bone.

27. A method of positioning an arthroplasty component relative to a bone, said method comprising the steps of providing an arthroplasty component having a tray portion with a first tab extending from one side of the tray portion, a second tab extending from another side of the tray portion, and a keel which extends from the tray portion at a location between the first and second tabs, engaging a first side of the bone with the first tab on the arthroplasty component, thereafter, pivoting the arthroplasty component about a location where the first tab engages the first side of the bone, moving the keel into the bone at a location between the first and second sides of the bone while performing said step of pivoting the arthroplasty component about the location where the first tab engages the first side of the bone, moving the second tab on the arthroplasty component along a second side of the bone while performing said step of pivoting the arthroplasty component about the location where the first tab engages the first side of the bone, and positioning the tray portion of the arthroplasty component over a portion of the bone disposed between the first and second sides of the bone while performing said step of pivoting the arthroplasty component about the location where the first tab engages the first side of the bone.

28. A method of positioning an arthroplasty component relative to a bone, said method comprising the steps of providing an arthroplasty component having a tray portion with a first tab extending from one side of the tray portion and a second tab extending from another side of the tray portion, the first tab having a first portion which is connected with the tray portion and extends transverse to the tray portion in a direction which is generally parallel to a central axis of the tray portion and a second portion which extends transverse to the first portion in a direction toward the central axis of the tray portion, engaging a first side of the bone with an end of the second portion of the first tab on the arthroplasty component, thereafter, pivoting the arthroplasty component about a location where the end of the second portion of the first tab engages the first side of the bone, said step of pivoting the arthroplasty component being at least partially performed with a portion of the bone disposed between the tray portion and the second portion of the first tab, moving the second tab on the arthroplasty component along a second side of the bone while performing said step of pivoting the arthroplasty component about the location where the second portion of the first tab engages the first side of the bone, and positioning the tray portion of the arthroplasty component over a portion of the bone disposed between the first and second sides of the bone while performing said step of pivoting the arthroplasty component about the location where the second portion of the first tab engages the first side of the bone, said step of positioning the tray portion of the arthroplasty component over a portion of the bone includes positioning the tray portion of the arthroplasty component over the portion of the bone disposed between the tray portion and the second portion of the first tab.

29. A method as set forth in claim 28 further including the step of moving a fastener through the second tab on the arthroplasty component and into the bone with a longitudinal central axis of the fastener extending at an acute angle to a side of the tray portion of the arthroplasty component.

30. A method as set forth in claim 28 further including the steps of moving a fastener through the second tab on the arthroplasty component, through a cortical portion of the bone on the second side of the bone, through a cancellous portion of the bone located between the first and second sides of the bone and into engagement with a cortical portion of the bone on the second side of the bone.

31. A method as set forth in claim 28 wherein the arthroplasty component has a keel which extends from the tray portion of the arthroplasty component at a location between the first and second tabs, said method further including the step of moving the keel into the bone at location between the first and second sides of the bone while performing said step of pivoting the arthroplasty component about the location where the first tab engages the first side of the bone.

32. A method as set forth in claim 31 further including the steps of moving a fastener through the second tab, through a portion of the bone, and into the keel to retain the arthroplasty component against movement relative to the bone.

33. A method as set forth in claim 31 further including the step of transmitting force from a fastener to the keel to urge the tray portion of the arthroplasty component toward the portion of the bone disposed between the first and second sides of the bone.

34. A method as set forth in claim 31 further including the step of moving a fastener into the keel along a path which is skewed at an acute angle to a side of the arthroplasty component.

35. A method as set forth in claim 28 wherein said step of moving the second tab on the arthroplasty component along the second side of the bone includes increasing area of engagement of the second tab with the second side of the bone during at least a portion of said step of pivoting the arthroplasty component about a location where the second portion of the first tab engages the first side of the bone.

36. A method as set forth in claim 28 further including interconnecting the portion of the bone disposed between the first and second sides of the bone and the tray portion of the arthroplasty component with bone cement.

37. A method as set forth in claim 36 wherein said step of interconnecting the portion of the bone disposed between the first and second sides of the bone and the tray portion of the arthroplasty component with bone cement includes filling a plurality of recesses in a side of the tray portion with bone cement to retard subsequent propagation of cracks through the bone cement.

* * * * *